United States Patent [19]

Spencer

[11] Patent Number: 4,986,138

[45] Date of Patent: Jan. 22, 1991

[54] SAMPLE INJECTION MEANS

[76] Inventor: R. Wilson Spencer, P.O. Box 22586, Houston, Tex. 77227

[21] Appl. No.: 435,563

[22] Filed: Nov. 13, 1989

Related U.S. Application Data

[63] Continuation-in-part of Ser. No. 287,344, Dec. 20, 1988, Pat. No. 4,879,915, which is a continuation of Ser. No. 26,824, Mar. 17, 1987, Pat. No. 4,791,821, which is a continuation-in-part of Ser. No. 720,166, Apr. 5, 1985, Pat. No. 4,651,574.

[51] Int. Cl.$^5$ .............................................. G01N 1/14
[52] U.S. Cl. .............................. 73/864.34; 73/863.83; 73/863.86
[58] Field of Search ........... 73/864.34, 864.35, 863.83, 73/863.84, 863.86, 864.73, 864.74, 864.51, 864.91, 863.81, 863.82, 863.85

[56] References Cited

U.S. PATENT DOCUMENTS

| | | |
|---|---|---|
| 1,669,776 | 5/1928 | Osburn . |
| 1,739,731 | 12/1929 | Osburne . |
| 1,842,134 | 1/1932 | Waite .................................. 141/283 |
| 2,475,857 | 7/1949 | Reinert .......................... 73/863.51 X |
| 2,693,705 | 11/1954 | Casler et al. ....................... 141/65 X |
| 2,797,150 | 6/1957 | Rigby .............................. 73/864.01 |
| 3,273,402 | 9/1966 | Farr ................................... 73/425.6 |
| 3,438,263 | 4/1969 | Cohen et al. ...................... 73/863.86 |
| 3,484,849 | 12/1969 | Huebner et al. ................ 141/329 X |
| 3,872,730 | 3/1975 | Ringrose et al. ............... 604/201 X |
| 3,940,993 | 3/1976 | Lapidot ........................ 73/864.34 X |
| 4,007,638 | 2/1977 | Irwin et al. ..................... 73/863.44 |
| 4,118,987 | 10/1978 | Zeh ................................. 73/863.61 |
| 4,174,632 | 11/1979 | Jansen ......................... 73/864.91 X |
| 4,306,581 | 12/1981 | Alandt ............................ 137/563 X |
| 4,454,773 | 6/1984 | Brunner et al. .............. 73/863.86 X |
| 4,532,959 | 8/1985 | Kaawn ........................... 141/285 X |
| 4,550,011 | 10/1985 | McCollum ............................ 422/68 |
| 4,616,515 | 10/1986 | Dancaine ...................... 73/863.83 X |
| 4,651,574 | 3/1987 | Spencer ....................... 73/864.74 X |
| 4,749,658 | 6/1988 | Jaekel et al. .................... 422/103 X |
| 4,769,154 | 9/1988 | Saylor et al. ................... 219/272 X |
| 4,791,821 | 12/1988 | Spencer ............................ 73/864.74 |
| 4,831,887 | 5/1989 | Crossley ........................ 73/864.34 |

FOREIGN PATENT DOCUMENTS

| | | | |
|---|---|---|---|
| 2204 | 6/1926 | Australia .............................. 141/285 |
| 86749 | 4/1959 | Denmark .......................... 73/863.61 |
| 46809 | 4/1889 | Fed. Rep. of Germany ...... 141/285 |
| 125201 | 11/1901 | Fed. Rep. of Germany ...... 141/285 |
| 286481 | 8/1915 | Fed. Rep. of Germany ...... 141/285 |
| 1203987 | 10/1965 | Fed. Rep. of Germany ... 73/863.81 |
| 104231 | 8/1981 | Japan . |
| 549706 | 6/1977 | U.S.S.R. . |

OTHER PUBLICATIONS

Patent Abstracts of Japan; ABS Grp No: P088; ABS vol. No: vol. 5, No. 175; ABS Pub. Date: Nov. 11, 1981.

Primary Examiner—Tom Noland
Attorney, Agent, or Firm—Robert C. Tucker; William David Kiesel

[57] ABSTRACT

A sample injection device is provided, comprising a vented needle having a body, the body having an upper end and a lower end, a point on the lower end, an injection passageway running axially through the body and communicating between the upper end and the lower end, and a vent passageway, running through the body and communicating between the lower end and the exterior of the body. The upper end of the body is connectable to a valve, and the lower end is connectable to a receptacle for receiving samples. When equipped with a circulating system and combined with a wheeled transport tank such as a railroad tank car or highway tank trailer having a reservoir, or a marine transport tank such as a barge, the invention enables the user to accomplish representative emission-free sampling of such transport containers and comprises a suction line extending into the reservoir; a pump having a suction port and a discharge port, the suction port being connected to the suction line; a discharge line connected to the discharge port; a sampling unit, for removing a sample from the discharge line, connected to the discharge line; a return line, connected on one end to the discharge line terminating within the reservoir.

8 Claims, 5 Drawing Sheets

SAMPLE INJECTION MEANS

RELATED APPLICATIONS

This is a continuation-in-part application of U.S. Pat. application, Ser. No. 287,344, filed on Dec. 20, 1988, and now U.S. Pat. No. 4,879,915 which is a continuation application of U.S. Pat. application, Ser. No. 26,824, filed on Mar. 17, 1987, and now U.S. Pat. No. 4,791,821, which is a continuation-in-part application of U.S. Pat. application Ser. No. 720,166, filed on Apr. 5, 1985 and now U.S. Pat. No. 4,651,574 by the inventor herein and entitled "Sample Injection Means", specific mention being made to obtain the benefit of the prior application's filing date.

BACKGROUND OF THE INVENTION

1. Field of the Invention

This invention relates to sampling devices and, more particularly, to devices which receive samples from a flowing fluid line, such as a process line.

2. Description of Prior Art

In many processes, such as those involved in manufacturing and industrial operations, it is imperative that samples be taken from lines of flowing fluid. It is desirable that such samples be taken so as to avoid contamination of the process, as well as to avoid contamination of the surrounding environment. Since a minimal disturbance of the process flow is also desirable, the sample is usually taken under pressure by tapping a conduit containing the flowing medium to be sampled. This is accomplished by tapping the process line with a sample line and providing a valve which can be opened to allow a sample of the fluid to escape into a sample receptacle. Because of the hazardous nature of many process fluids, it is desirable that human contact with the sample be minimized.

Examples of patented sampling devices may be seen by examining the following patents, which are in herein by reference:

U.S. Pat. No. 2,844,964 (Guibert)
U.S. Pat. No. 2,693,705 (Casler)
U.S. Pat. No. 3,276,265 (Taft)
U.S. Pat. No. 3,383,923 (Conche, et al)
U.S. Pat. No. 3,872,730 (Ringrose)
U.S. Pat. No. 4,014,216 (Thorton, et al)
U.S. Pat. No. 4,118,987 (Zeh)
U.S. Pat. No. 4,174,632 (Jansen)
U.S. Pat. No. 4,380,176 (Bauer, et al)
U.S.S.R. Patent No. 549,706

From an examination of the above listed patents, it will become apparent that it is generally known to provide a sampling mechanism whereby sample fluid from a valve passes through a hollow needle, which is inserted through a septum in a removable sample container, thus filing the container. Because a substantial seal is created between the septum and the needle, a vent must be provided in the sample container in order for fluid under pressure to safely enter the container. In Jansen and Zeh, listed above, the vent is provided by a second needle.

The two needle approach described above has proven to be unsatisfactory. By puncturing the septum twice, there is a greater possibility of leakage should the sample container be over-filled. Substances, such as hazardous acids, etc., would then contaminate and possibly damage process equipment, pollute the environment and possibly injure the personnel involved in collecting the sample. Also, the needles disclosed in the prior art are beveled so as to produce a sharp edge which cuts as it penetrates a septum. This cutting action results in a poor seal between the needle and the septum, further resulting in an increased probability of leakage. Also, the presence of two needles has created the problem of multiple punctures in the septum as a sample container is repeatedly removed and then reinstalled. Looking at the Zeh patent, for example, if the sample container were rotated slightly and then reinstalled, the needles would pierce the septum at different points, resulting in leakage through the original puncture holes in the septum. The Jansen device attempted to solve this problem by providing side-by-side needles which are centered so as to pierce the septum in the same place, regardless of the rotational position of the sample container. This arrangement has also proven unsatisfactory, in that an inadequate seal is formed when the two needles are inserted into the same puncture hole.

Stringent environmental regulations have resulted from an increasing concern over the safety of sampling personnel is well as discharge of hazardous materials to the atmosphere. Regulatory and safety concerns have thus severely limited sampling, resulting in elaborate and expensive containment schemes. Nevertheless, monitoring of industrial processes must still take place. Liquid sampling of highway tank trailers, railroad tank cars, and marine transport tanks such as tankers and barges is still performed by an operator dipping a container into the tank reservoir and exposing himself to the fluid being sampled. The prior art devices have not managed to economically provide the necessary safety while maintaining the integrity of the sample.

SUMMARY OF THE INVENTION

Accordingly, it is an object of this invention to provide a sample injection means which minimizes sample leakage while allowing adequate venting of the sample container.

It is another object of this invention to provide a sample injection means which penetrates a septum with a single needle, and which minimizes the cutting of the septum.

It is another object of this invention to provide a sample extraction system which will operate in combination with a wheeled transport tank or marine transport tank, providing a means for readily sampling the contents of the tank.

It is yet a further object of this invention to provide a sample extraction system which will accomplish all of the above objectives.

Therefore, a sample injection means is provided, comprising a vented needle having a body, the body having an upper end and a lower end, a point on the lower end, an injection passageway running axially through the body and communicating between the upper end and the lower end, and a vent passageway, running through the body and communicating between the lower end and the exterior of the body. The upper end of the body is connectable to a valve and the lower end is connectable to a receptacle for receiving samples.

When equipped with a circulating system and combined with a wheeled transport tank or marine transport tank such as a railroad tank car, a highway tank trailer, or marine barge having a reservoir, the invention enables the user to accomplish representative emission-free sampling of such transport containers and comprises a suction line extending into the reservoir; a pump having a suction port and a discharge port, the suction port being connected to the suction line; a discharge line connected to the discharge port; a sampling unit, for removing a sample from the discharge line, connected to the discharge line; a return line, connected on one end to the discharge line and terminating within the reservoir.

The above and other objectives and advantages of the invention will become apparent from the following description when considered with the accompanying drawings.

DETAILED DESCRIPTION OF THE PREFERRED EMBODIMENTS OF THE INVENTION

Figures 1, 2:
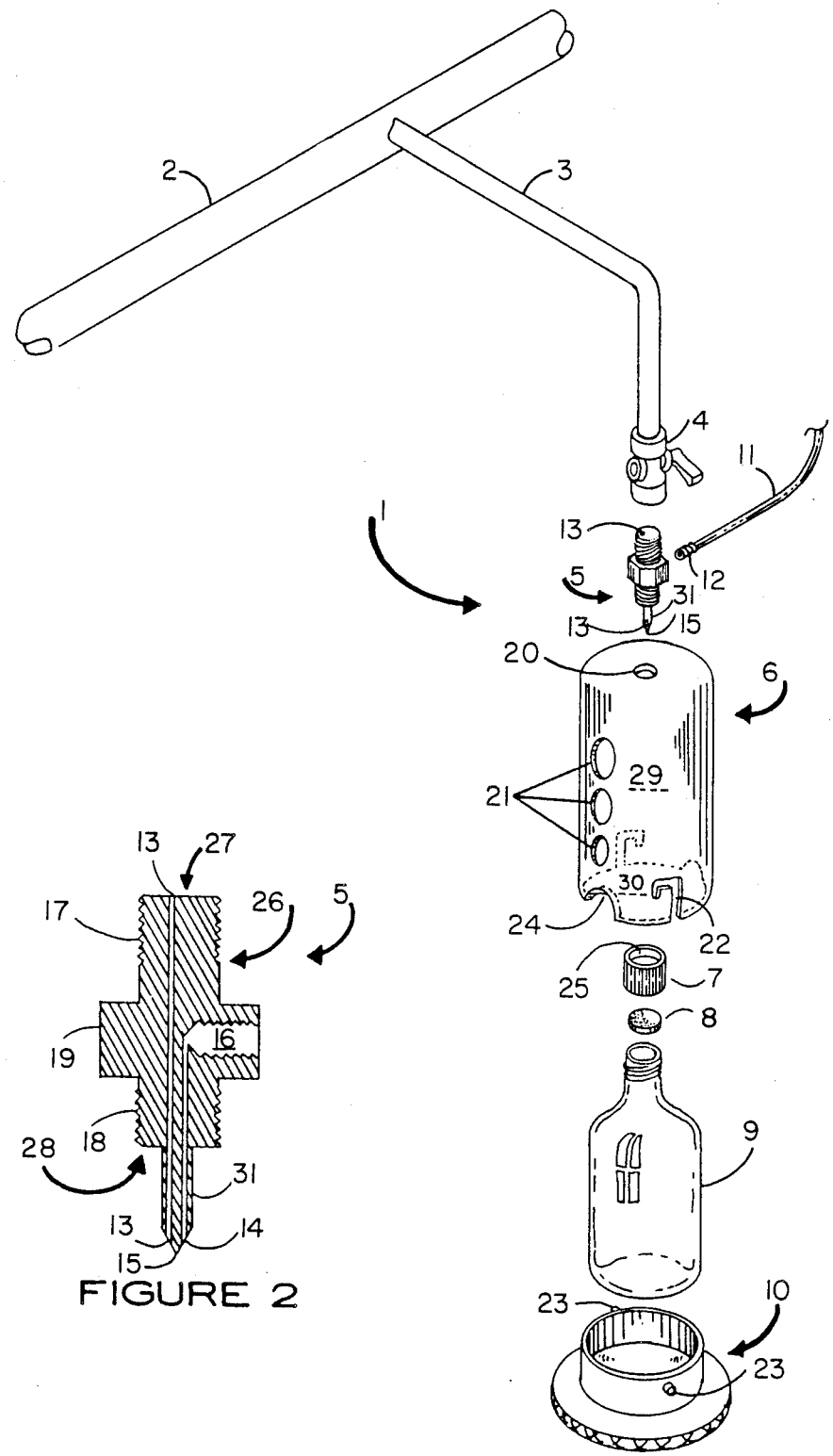
FIG. 1 is an exploded perspective view of a preferred embodiment of the invention.
FIG. 2 is a sectional view of a preferred embodiment of the invention.

As shown in FIG. 1, the sample injection means 1 is connectable to a process line 2 by means of a sample line 3 and valve 4. A vented needle 5 is connectable to the valve 4, preferably by a threaded valve fitting 17.

As shown in greater detail in FIG. 2, the vented needle 5 comprises a solid body 26 having an upper end 27 and a lower end 28. A needle shaft 31, preferably cylindrical, is machined onto lower end 28. At the end of needle shaft 31 is a point 15, which is preferably conical in shape, and preferably forming an acute angle of twenty degrees with the longitudinal axis of the needle 5. Threaded shroud fitting 18 is machined onto lower end 28 for attachment to a shielding means, such as shroud 6. Injection passageway 13 transmits sample fluid through the needle 5. Vent passageway 14 vents gases and excess sample fluids from the sample bottle 9 to vent line opening 16, to which may be attached a vent line fitting 12, which, in turn, is attachable to a vent line 11. Vent line 11 may lead to a closed waste container or may be coupled with valving and a pressure reducing mechanism, such as a venturi, in order to return the contents of the vent line 11 to the process line 2. Wrench fitting 19 may be machined onto needle 5 as shown, to facilitate installation.

As can be seen, point 15 will penetrate a septum 8 in opening 25 of sample bottle cap 7. The conical shape of point 15, coupled with the location of the emergence of passageways 13 and 14 above the point 15, minimizes the cutting of the septum 8 which occurs with prior art devices. It is preferable for effective sealing, that septum 8 be composed of chemically resistant elastomers of the chemical group hexafluoropropylene vinylidene fluoride. Septums of natural rubber, buna-n (nitride), silicone, buna-s or neoprene are much less effective. Also, it has been found that a septum thickness of ⅛ inch is preferable.

As a safety measure, a shroud 6 may be provided. A top opening 20 in shroud 6 receives shroud fitting 18. Shroud 6 should envelope sample bottle 9 in order to provide a maximum shield from sample spillage or bottle breakage. Bottom opening 30 in shroud 6 allows for insertion of sample bottle 9. Shroud cavity 29 may be shaped so a to accommodate various sizes of sample bottles 9. However, it is preferred that cavity 29 closely correspond to the external dimensions of bottle 9 so as to assure the centering of bottle 9, and thus the centering of point 15 so as to penetrate septum 8 in the same place regardless of the degree of rotation of bottle 9. Inspection ports 21 are provided to aid in preventing over-filling of bottle 9 while maximizing the shielding effect o shroud 6. Bottle handling slots 24 are provided to aid in installation and removal of sample bottles 9.

Shroud cap 10 provides a closure for bottom opening 30, assuring maximum safety. Shroud cap 10 is removably attachable to shroud 6, by means of locking pins 23 and j-slots 22.

Figure 3:
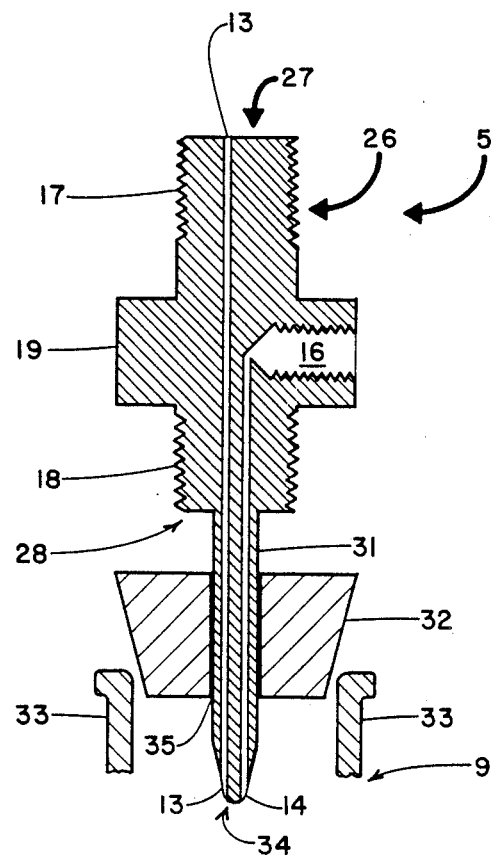
FIG. 3 is a sectional view of a preferred embodiment of the invention.

In applications where a septum 8 is not needed or is not dictated by safety considerations, the needle embodiment shown in FIG. 3 will provide an efficient means for sampling, while eliminating septum 8. As can be seen, a resilient stopper 32 is fitted about needle shaft 31. Preferably, stopper 32 is provided with an opening 35 therein which opening 35 is of a slightly smaller diameter than shaft 31, ensuring a tight fit while enabling the easy replacement of stopper 32. Thus, a sample bottle 9 (not shown entirely in FIG. 3) having mouth 33 may simply be thrust onto stopper 32 for sampling. Upon removal, a separate stopper may be used to seal bottle 9. In such situations a threaded bottle mouth and threaded bottle cap (as shown in FIG. 1) are eliminated. Shroud 6 and shroud cap 10 may be utilized as previously described. In this embodiment, tip 34 of shaft 31 may comprise a blunt or rounded (as shown in FIG. 3) tip for safety, since it is not necessary to puncture a septum.

Thus, as can be seen, a sample injection means 1 is provided which accomplishes sampling and venting with a single vented needle 5, resulting in safer, more efficient sampling. Environmental contamination is minimized. By providing venting outside of shroud 6, contamination of the exterior of sample bottle 9 is also reduced. Vented needle 5 is easily adaptable to fit many sampling devices. Applications for the device include the sampling of hazardous materials and known carcinogens such as benzene, carbon tetrachloride, sulfuric acid and the like; fuming materials, such as monochloracetic acid; and biological compounds, such as gene-spliced microorganisms.

Figure 4:
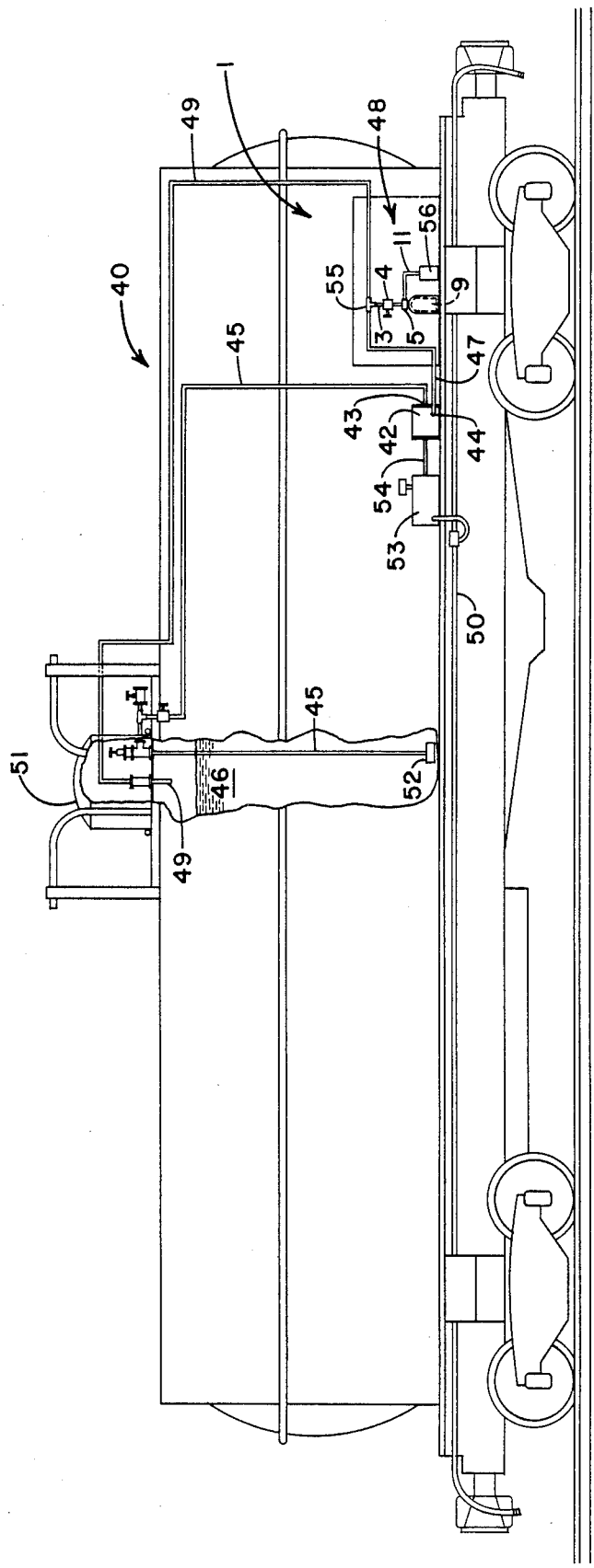
FIG. 4 is a side view of an embodiment of the invention in place on a railroad tank car.
Figure 5:
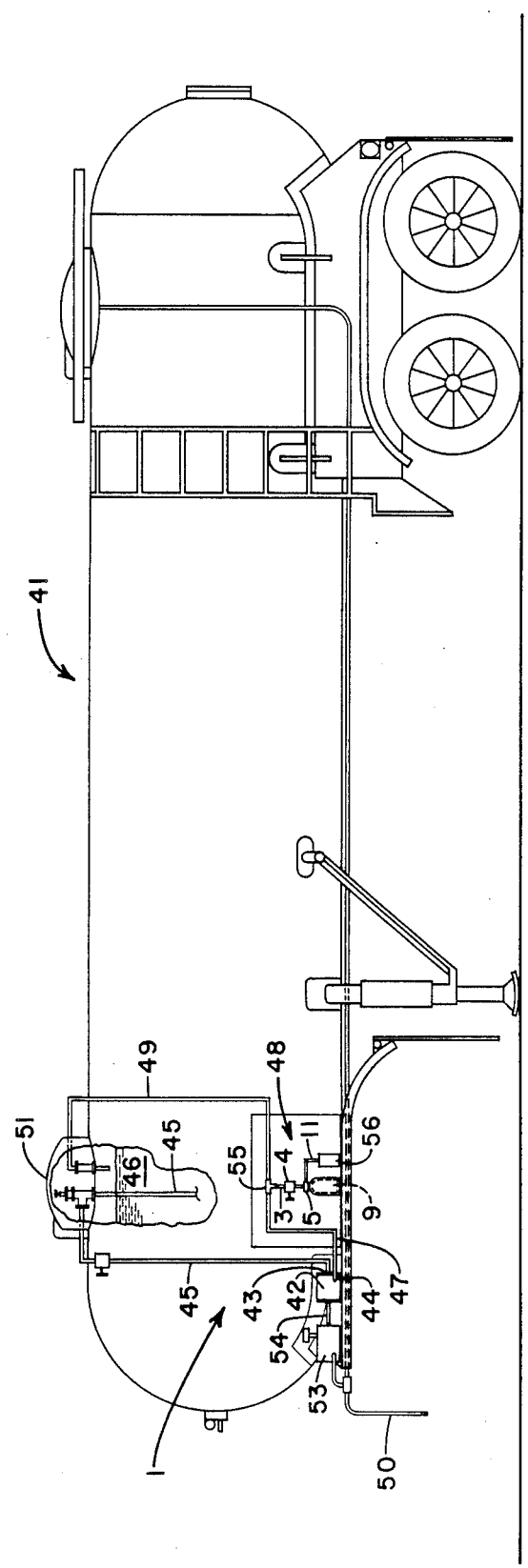
FIG. 5 is a side view of an embodiment of the invention in place on a highway tank trailer.
Figure 6:
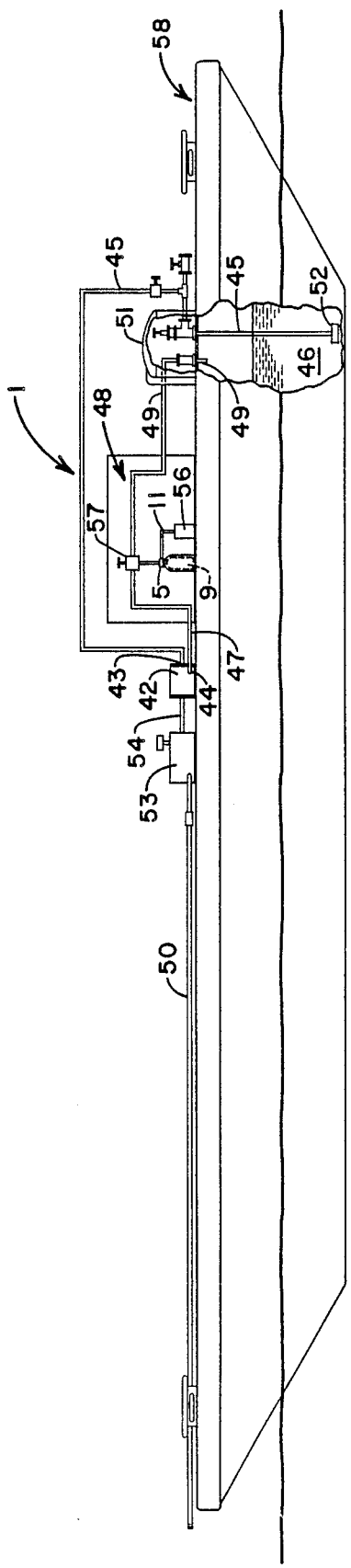
FIG. 6 is a side view of an embodiment of the invention in place on a marine barge.

A modified version of the system 1 may be used for closed loop sampling of fluids carried by wheeled transport tanks or marine transport tanks. For the purposes herein, the term "wheeled transport tanks" shall include railroad tank cars 40, such as the one shown in FIG. 4, and highway tank trailers 41, such as the one shown in FIG. 5. The term "marine transport tank" shall include marine tankers or barges, such as the one shown in FIG. 6. Each wheeled transport tank 40, 41 or marine transport tank 58 includes a reservoir 46. As shown in FIGS. 4–6, the system 1 must additionally include a circulating means such as a pump 42 having a suction port 43 and a discharge port 44, from reservoir 46. Suction line 45 runs from within reservoir 46 to suction port 43. Discharge line 47 runs from discharge port 44 to a sampling means 48. A return line 49 runs from sampling means 48 back to reservoir 46. The embodiment of sampling means 48 shown in FIGS. 4 and 5 is connected between discharge line 47 and return line 48 by tee 55. As shown in FIG. 6, tee 55 and sample line 3 may be eliminated by substituting a three-way valve 57 for two-way valve 4. A sample container such as sample bottle 9 is removably connectable to sampling means 48, as described previously in greater detail.

As shown in FIGS. 4–6, access to the interior of reservoir 46 may be gained through existing hatches 51. Existing valves, piping and fittings on wheeled transport tanks 40,41 may form parts of suction line 45 and return line 49. It may be desirable to furnish a filter screen 52 at the end of suction line 45, as shown. Since pressurized gas lines 50 are usually available on wheeled transport tanks 40, 41, as well as some marine transport tanks 58, it is desirable that an air motor 53 be furnished to drive pump 42 via a coupling, such as a magnetic coupling 54. Sampling means 48 may include sample line 3, valve 4, vented needle 5 and vent line 11, or other means known in the art, such as other embodiments of the invention 1 more particularly described herein. Vent line 11 is shown connected to a waste canister 56 to ensure emission-free sampling.

While it is preferable that all components of the system 1 be attached to wheeled transport tanks 40, 41, or marine transport tanks 58, this is not a necessity. For example, the entire sampling system 1 could be remotely mounted so as to couple to transport tanks 40, 41, 58 only when sampling is required. However, due to governmental body sampling requirements as well as other practical considerations, it is usually preferable that the system 1 be fixedly attached to wheeled transport tanks 40, 41, 58.

Operation of the system 1 shown in FIGS. 4–6 is simple. Air motor 53 is activated, establishing flow through the system 1. If desired, valve 4 is initially closed to cause initial flow to bypass sampling means 48 until a homogeneous, representative sample flow is established. If three-way valve 57 is utilized as shown in FIG. 6, it is simply set in a mode to bypass sampling means 48. Valve 4 is then opened so as to allow sample flow to enter sampling means 48. Sampling means 48 is operated in the normal manner described herein, depositing a sample in sample bottle 9, with vented vapors being entrained and/or filtered by waste canister 56. Thus, prior art "dipping" into reservoir 46 is eliminated, and exposure of the environment and sampling personnel to the sample fluid is minimized.

While the above embodiments of the invention have been defined in specific terms, it will be obvious to those skilled in the art that variation may be made without departing from the spirit and scope of the invention, as defined by the following claims.

I claim:

1. In combination with a wheeled transport tank having a reservoir, a sample extraction system, comprising:
   a. a suction line fixedly attached to said wheeled transport tank and extending into said reservoir;
   b. a pump fixedly attached to said wheeled transport tank and having a suction port and a discharge port, said suction port being connected to said suction line;
   c. a discharge line fixedly attached to said wheeled transport tank and connected to said discharge port;
   d. a valve, connected to said discharge line;
   e. a sample injection means, for receiving a sample from said discharge line, said sample injection means including a single vented needle having a body, said body having an upper end and a lower end, a needle shaft extending from said lower end, said shaft having a tip thereon, an injection passageway running through said body and communicating between the exterior of said body above said shaft and the exterior of said shaft, and a vent passageway, running through said body and communicating between the exterior of said body above said shaft and the exterior of said shaft, said sample injection means being connected at said upper end to said valve;
   f. a return line, fixedly attached to said wheeled transport tank and connected on one end to said discharge line and terminating within said reservoir; and
   g. a sample container, removably connectable to said sample injection means.

2. A sample extraction system according to claim 1, further comprising:
   h. an air motor, fixedly attached to said wheeled transport tank and operatively connected to said pump.

3. In combination with a wheeled transport tank having a reservoir, a sample extraction system, comprising:
   a. a suction line fixedly attached to said wheeled transport tank and extending into said reservoir;
   b. a pump fixedly attached to said wheeled transport tank and having a suction port and a discharge port, said suction port being connected to said suction line;
   c. a discharge line fixedly attached to said wheeled transport tank and connected to said discharge port;
   d. a sampling means, for removing a sample from said discharge line, fixedly attached to said wheeled transport tank and connected to said discharge line;
   e. a return line fixedly attached to said wheeled transport tank and connected to one end to said discharge line and terminating within said reservoir; and
   f. a sample container, removably connectable to said sampling means.

4. A sample extraction system according to claim 1, further comprising:
   i. a vent line connectable to said needle body so as to communicate with said vent passageway; and
   j. a waste canister, connected to said vent line.

5. In combination with a marine transport tank having a reservoir, a sample extraction system, comprising:
   a. a suction line fixedly attached to said marine transport tank and extending into said reservoir;
   b. a pump fixedly attached to said marine transport tank and having a suction port and a discharge port, said suction port being connected to said suction line;
   c. a discharge line fixedly attached to said marine transport tank and connected to said discharge port;
   d. a sampling means, for removing a sample from said discharge line, fixedly attached to said marine transport tank and connected to said discharge line;
   e. a return line, fixedly attached to said marine transport tank and connected on one end to said discharge line and terminating within said reservoir; and
   f. a sample container, removably connectable to said sampling means.

6. In combination with a marine transport tank having a reservoir, a sample extraction system, comprising:
   a. a suction line fixedly attached to said marine transport tank and extending into said reservoir;
   b. a pump fixedly attached to said marine transport tank and having a suction port and a discharge port, said suction port being connected to said suction line;
   c. a discharge line fixedly attached to said marine transport tank and connected to said discharge port;
   d. a valve, connected to said discharge line;
   e. a sample injection means, for receiving a sample from said discharge line, said sample injection means including a single vented needle having a body, said body having an upper end and a lower end, a needle shaft extending from said lower end, said shaft having a tip thereon, an injection passageway running through said body and communicating between the exterior of said body above said shaft and the exterior of said shaft, and a vent passageway, running through said body and communicating between the exterior of said body above said shaft and the exterior of said shaft, said sample injection means being connected at said upper end to said valve;
   f. a return line, fixedly attached to said marine transport tank and connected on one end to said discharge line and terminating within said reservoir; and
   g. a sample container, removably connectable to said sample injection means.

7. A sample extraction system according to claim 6, further comprising:
   h. an air motor, fixedly attached to said marine transport tank and operatively connected to said pump.

8. A sample extraction system according to claim 6, further comprising:
   i. a vent line connectable to said needle body so as to communicate with said vent passageway; and
   j. a waste canister, connected to said vent line.

* * * * *